(12) United States Patent
Wang et al.

(10) Patent No.: US 9,072,590 B2
(45) Date of Patent: Jul. 7, 2015

(54) SHEATHS REDUCING RECOIL AND LOSS OF RETENTION FOR POLYMER SCAFFOLDS CRIMPED TO BALLOONS

(71) Applicant: Abbott Cardiovascular Systems Inc., Santa Clara, CA (US)

(72) Inventors: Yunbing Wang, Sunnyvale, CA (US); Jhoan Bayogo, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 241 days.

(21) Appl. No.: 13/708,638

(22) Filed: Dec. 7, 2012

(65) Prior Publication Data

US 2014/0157567 A1 Jun. 12, 2014

(51) Int. Cl.
| A61F 2/00 | (2006.01) |
| A61F 2/958 | (2013.01) |
| A61F 2/97 | (2013.01) |
| B23P 11/00 | (2006.01) |
| A61F 2/95 | (2013.01) |
| A61F 2/01 | (2006.01) |

(52) U.S. Cl.
CPC .......... *A61F 2/0095* (2013.01); *Y10T 29/49826* (2015.01); *B23P 11/005* (2013.01); *A61F 2002/9522* (2013.01); *A61F 2002/011* (2013.01); *A61F 2/958* (2013.01); *A61F 2/97* (2013.01); *A61F 2250/0059* (2013.01)

(58) Field of Classification Search
CPC .. B23P 11/005; B23P 17/00; B23P 2002/011; B23P 2002/9522; B23P 2/962; B23P 2/97; B23P 2250/0059; A61F 2002/011; A61F 2002/9522; A61F 2/962; A61F 2/97; A61F 2250/0059; A61F 2/0095

USPC .......... 29/407.01, 423–424, 506, 508, 522.1, 29/523, 446, 450, 451, 469; 623/1.12
See application file for complete search history.

(56) References Cited

U.S. PATENT DOCUMENTS

| 4,243,050 A | 1/1981 | Littleford |
| 4,581,025 A | 4/1986 | Timmermans |
| 4,710,181 A | 12/1987 | Fuqua |
| 5,015,231 A | 5/1991 | Keith et al. |
| 5,158,545 A | 10/1992 | Trudell et al. |
| 5,211,654 A | 5/1993 | Kaltenbach |
| 5,250,033 A | 10/1993 | Evans et al. |
| 5,352,236 A | 10/1994 | Jung et al. |
| 5,458,615 A | 10/1995 | Klemm et al. |
| 5,545,211 A | 8/1996 | An et al. |

(Continued)

FOREIGN PATENT DOCUMENTS

| WO | WO 98/39056 | 9/1998 |
| WO | WO 02/060345 | 8/2002 |
| WO | WO 2011/094048 | 8/2011 |

OTHER PUBLICATIONS

U.S. Appl. No. 13/644,347, filed Oct. 4, 2012, Wang.

*Primary Examiner* — David Bryant
*Assistant Examiner* — Matthew P Travers
(74) *Attorney, Agent, or Firm* — Squire Patton Boggs (US) LLP

(57) ABSTRACT

A medical device includes a polymer scaffold crimped to a catheter having an expansion balloon. A single piece sheath is placed over the scaffold immediately following crimping of the scaffold to the balloon. The single piece sheath is replaced by a two-piece sheath, which is removed prior to performing a medical procedure using the medical device.

23 Claims, 9 Drawing Sheets

(56) References Cited

U.S. PATENT DOCUMENTS

| | | |
|---|---|---|
| 5,569,294 A | 10/1996 | Parkola |
| 5,591,226 A | 1/1997 | Trerotola et al. |
| 5,647,857 A | 7/1997 | Anderson et al. |
| 5,653,697 A | 8/1997 | Quiachon et al. |
| 5,693,066 A | 12/1997 | Rupp et al. |
| 5,709,703 A | 1/1998 | Lukic et al. |
| 5,749,852 A | 5/1998 | Schwab et al. |
| 5,765,682 A | 6/1998 | Bley et al. |
| 5,776,141 A | 7/1998 | Klein et al. |
| 5,782,855 A | 7/1998 | Lau et al. |
| 5,817,100 A | 10/1998 | Igaki |
| 5,868,707 A | 2/1999 | Williams et al. |
| 5,893,868 A | 4/1999 | Holman et al. |
| 5,964,730 A | 10/1999 | Williams et al. |
| 6,010,529 A | 1/2000 | Herweck et al. |
| 6,110,146 A | 8/2000 | Berthiaume et al. |
| 6,132,450 A | 10/2000 | Hanson et al. |
| 6,152,944 A | 11/2000 | Holman et al. |
| 6,197,016 B1 | 3/2001 | Fourkas et al. |
| 6,254,609 B1 | 7/2001 | Vrba et al. |
| 6,334,867 B1 | 1/2002 | Anson |
| 6,342,066 B1 | 1/2002 | Toro et al. |
| 6,355,013 B1 | 3/2002 | Van Muiden |
| 6,416,529 B1 | 7/2002 | Holman et al. |
| 6,447,540 B1 | 9/2002 | Fontaine et al. |
| 6,533,806 B1 | 3/2003 | Sullivan et al. |
| 6,749,584 B2 | 6/2004 | Briggs et al. |
| 6,783,542 B2 | 8/2004 | Eidenschink |
| 6,790,224 B2 | 9/2004 | Gerberding |
| 6,805,703 B2 | 10/2004 | McMorrow |
| 6,827,731 B2 | 12/2004 | Armstrong et al. |
| 6,899,727 B2 | 5/2005 | Armstrong et al. |
| 7,198,636 B2 | 4/2007 | Cully et al. |
| 7,314,481 B2 | 1/2008 | Karpiel |
| 7,347,868 B2 | 3/2008 | Burnett et al. |
| 7,384,426 B2 | 6/2008 | Wallace et al. |
| 7,618,398 B2 | 11/2009 | Holman et al. |
| 7,998,404 B2 | 8/2011 | Huang et al. |
| 8,414,528 B2 | 4/2013 | Liu et al. |
| 8,539,663 B2 | 9/2013 | Wang et al. |
| 8,752,265 B2 | 6/2014 | Wang |
| 2001/0001128 A1 | 5/2001 | Holman et al. |
| 2002/0052640 A1 | 5/2002 | Bigus et al. |
| 2002/0099431 A1 | 7/2002 | Armstrong et al. |
| 2003/0004561 A1 | 1/2003 | Bigus et al. |
| 2003/0212373 A1 | 11/2003 | Hall et al. |
| 2004/0073286 A1 | 4/2004 | Armstrong et al. |
| 2004/0143315 A1 | 7/2004 | Bruunn et al. |
| 2004/0260379 A1* | 12/2004 | Jagger et al. .............. 623/1.11 |
| 2006/0009832 A1* | 1/2006 | Fisher .................. 623/1.11 |
| 2006/0015171 A1 | 1/2006 | Armstrong et al. |
| 2007/0289117 A1* | 12/2007 | Huang et al. .................. 29/508 |
| 2008/0010947 A1 | 1/2008 | Huang et al. |
| 2009/0105800 A1* | 4/2009 | Sabaria ..................... 623/1.11 |
| 2009/0221965 A1 | 9/2009 | Osypka |
| 2010/0004735 A1 | 1/2010 | Yang et al. |
| 2011/0184509 A1 | 7/2011 | Von Oepen et al. |
| 2012/0042501 A1 | 2/2012 | Wang et al. |
| 2012/0109281 A1 | 5/2012 | Papp |
| 2012/0261858 A1 | 10/2012 | Roberts et al. |
| 2012/0285609 A1 | 11/2012 | Wang |
| 2012/0302955 A1 | 11/2012 | Liu et al. |
| 2012/0324696 A1 | 12/2012 | Liu et al. |
| 2014/0096357 A1 | 4/2014 | Wang |
| 2014/0157567 A1 | 6/2014 | Wang |
| 2014/0379064 A1 | 12/2014 | Pacetti et al. |

* cited by examiner

SHEATHS REDUCING RECOIL AND LOSS OF RETENTION FOR POLYMER SCAFFOLDS CRIMPED TO BALLOONS

FIELD OF THE INVENTION

The present invention relates to medical devices; more particularly, the invention relates to sheaths for polymeric scaffolds crimped to a delivery balloon.

BACKGROUND OF THE INVENTION

A variety of non-surgical interventional procedures have been developed over the years for opening stenosed or occluded blood vessels in a patient caused by the build up of plaque or other substances on the walls of the blood vessel. Such procedures usually involve the percutaneous introduction of an interventional device into the lumen of the artery. In one procedure the stenosis can be treated by placing an expandable interventional device such as an expandable stent into the stenosed region to hold open and sometimes expand the segment of blood vessel or other arterial lumen. Metal or metal alloy stents have been found useful in the treatment or repair of blood vessels after a stenosis has been compressed by percutaneous transluminal coronary angioplasty (PTCA), percutaneous transluminal angioplasty (PTA) or removal by other means. Metal stents are typically delivered in a compressed condition to the target site, then deployed at the target into an expanded condition or deployed state to support the vessel.

The following terminology is used. When reference is made to a "stent", this term will refer to a metal or metal alloy structure, generally speaking, while a scaffold will refer to a polymer structure. It is understood, however, that the art sometimes uses the term "stent" when referring to either a metal or polymer structure.

Metal stents have traditionally fallen into two general categories—balloon expanded and self-expanding. The later type expands to a deployed or expanded state within a vessel when a radial restraint is removed, while the former relies on an externally-applied force to configure it from a crimped or stowed state to the deployed or expanded state.

Self-expanding stents formed from, for example, shape memory metals or super-elastic alloys such as nickel-titanium (NiTi) which are designed to automatically expand from a compressed state when the radial restraint is withdrawn or removed at the distal end of a delivery catheter into the body lumen, i.e. when the radial restraint is withdrawn or removed. Typically, these stents are delivered within a radially restraining polymer sheath. The sheath maintains the low profile needed to navigate the stent towards the target site. Once at the target site, the sheath is then removed or withdrawn in a controlled manner to facilitate deployment or placement at the desired site. Examples of self-expanding stents constrained within a sheath when delivered to a target site within a body are found in U.S. Pat. No. 6,254,609, US 20030004561 and US 20020052640.

Balloon expanded stents, as the name implies, are expanded upon application of an external force through inflation of a balloon, upon which the stent is crimped. The expanding balloon applies a radial outward force on the luminal surfaces of the stent. During the expansion from a crimped or stowed, to deployed or expanded state the stent undergoes a plastic or irreversible deformation in the sense that the stent will essentially maintain its deformed, deployed state after balloon pressure is withdrawn.

Balloon expanded stents may also be stored within a sheath, either during a transluminal delivery to a target site or during the assembly or in the packaging of the stent-balloon catheter delivery system. The balloon expanded stent may be contained within a sheath when delivered to a target site to minimize dislodgment of the stent from the balloon while en route to the target vessel. Sheaths may also be used to protect a drug eluting stent during a crimping process, which presses or crimps the stent to the balloon catheter. When an iris-type crimping mechanism, for example, is used to crimp a stent to balloon, the blades of the crimper, often hardened metal, can form gouges in a drug-polymer coating or even strip off coating through interaction similar to forces at play when the blades and/or stent struts are misaligned during the diameter reduction. Examples of stents that utilize a sheath to protect the stent during a crimping process are found in U.S. Pat. No. 6,783,542 and U.S. Pat. No. 6,805,703.

A polymer scaffold, such as that described in US 20100004735 may be made from a biodegradable, bioabsorbable, bioresorbable, or bioerodable polymer. The terms biodegradable, bioabsorbable, bioresorbable, biosoluble or bioerodable refer to the property of a material or stent to degrade, absorb, resorb, or erode away after the scaffold has been implanted at the target vessel. The polymer scaffold described in US 20100004735, as opposed to a metal stent, is intended to remain in the body for only a limited period of time. In many treatment applications, the presence of a stent in a body may be necessary for a limited period of time until its intended function of, for example, maintaining vascular patency and/or drug delivery is accomplished. Moreover, it is believed that biodegradable scaffolds, as opposed to a metal stent, allow for improved healing of the anatomical lumen and reduced incidence of late stent thrombosis. For these reasons, there is a desire to treat a vessel using a polymer scaffold, in particular a bioerodible polymer scaffold, as opposed to a metal stent, so that the prosthesis's presence in the vessel is for a limited duration. However, there are numerous challenges to overcome when developing a delivery system having a balloon-expanded polymer scaffold.

Polymer material considered for use as a polymeric scaffold, e.g. poly(L-lactide) ("PLLA"), poly(L-lactide-co-glycolide) ("PLGA"), poly(D-lactide-co-glycolide) or poly(L-lactide-co-D-lactide) ("PLLA-co-PDLA") with less than 10% D-lactide, and PLLD/PDLA stereo complex, may be described, through comparison with a metallic material used to form a stent, in some of the following ways. A suitable polymer has a low strength to weight ratio, which means more material is needed to provide an equivalent mechanical property to that of a metal. Therefore, struts must be made thicker and wider to have the required strength for a stent to support lumen walls at a desired radius. The scaffold made from such polymers also tends to be brittle or have limited fracture toughness. The anisotropic and rate-dependant inelastic properties (i.e., strength/stiffness of the material varies depending upon the rate at which the material is deformed) inherent in the material only compound this complexity in working with a polymer, particularly, bio-absorbable polymer such as PLLA or PLGA. Challenges faced when securing a polymer scaffold to a delivery balloon, and achieving uniform deployment of the scaffold are discussed in U.S. patent application Ser. No. 13/644,347.

When using a polymer scaffold, several of the accepted processes for metal stent handling can no longer be used. A metal stent may be crimped to a balloon in such a manner as to minimize, if not eliminate recoil in the metal structure after removal from the crimp head. Metal materials used for stents are generally capable of being worked more during the crimping process than polymer materials. This desirable property of the metal allows for less concern over the metal stent-balloon engagement changing over time when the stent-catheter is packaged and awaiting use in a medical procedure. Due to the material's ability to be worked during the crimping process, e.g., successively crimped and released at high temperatures within the crimp mechanism, any propensity for elastic recoil in the material following crimping can be significantly reduced, if not eliminated, without affecting the stent's radial strength when later expanded by the balloon. As such, following a crimping process the stent-catheter assembly often does not need packaging or treatment to maintain the desired stent-balloon engagement and delivery profile. If the stent were to recoil to a larger diameter, meaning elastically expand to a larger diameter after the crimping forces are withdrawn, then significant dislodgment force could be lost and the stent-balloon profile not maintained at the desired diameter needed to deliver the stent to the target site.

While a polymer scaffold may be formed so that it is capable of being crimped in such a manner as to reduce inherent elastic recoil tendencies in the material when crimped, e.g., by maintaining crimping blades on the scaffold surface for an appreciable dwell period, the effectiveness of these methods are limited. Significantly, the material generally is incapable of being worked to the degree that a metal stent may be worked without introducing deployed strength problems, such as excessive cracking in the material. Recoil of the crimped structure, therefore, is a problem that needs to be addressed.

In view of the foregoing, there is a need to address the challenges associated with securing a polymer scaffold to a delivery balloon and maintaining the integrity of a scaffold-balloon catheter delivery system up until the time when the scaffold and balloon are delivered to a target site within a body, and to be able to uniformly deploy the scaffold through balloon pressurization within a vessel.

SUMMARY OF THE INVENTION

The invention is directed to sheaths used to maintain polymer scaffold-balloon engagement and delivery system profile while, at the same time, avoiding adverse effects on balloon deployment and balloon integrity when a sheath is placed over and/or removed from a crimped scaffold and balloon as the delivery system is assembled or prior to preforming a medical procedure. In a preferred embodiment methods of the invention include methods for fitting a sheath over a scaffold without damage to the balloon, particularly for longer scaffold (equal to, or longer than 18 mm in length). According to this aspect a method is disclosed for placing a sheath specially made to apply an inward compressive force on a scaffold shortly after the scaffold is crimped to a balloon. This inward force reduces recoil and maintains a scaffold retention on the balloon.

Sheaths and methods of applying sheaths according to the invention are particularly useful for avoiding disruption to a scaffold-balloon arrangement, and in particular avoiding balloon bunching near a proximal end of the balloon. Scaffolds formed near to, or greater than a deployed diameter may exhibit an excessive propensity for elastic recoil following the crimping process, due to the shape memory in the material. Thus, the scaffold tends to return back to its pre-crimp diameter due to recoil. Recoil both increases the crossing profile and reduces the scaffold-balloon engagement needed to hold the scaffold on the balloon.

To minimize recoil, a single-piece sheath is placed over the crimped scaffold immediately following crimping. It has been discovered, however, that a single piece sheath can cause disruption to the balloon when it is pushed from the distal to proximal end of the balloon after crimping especially for scaffolds that are greater than about 18 mm in length. This results in the proximal balloon end forming bunched or compressed balloon material, which can result in failure or collapse of the balloon. As a consequence, the scaffold may not be able to correctly deploy due to damage to the balloon.

However, it was discovered that a sheath formed with flared or fluted ends on both ends and/or placed between the balloon proximal end and the proximal end of the catheter (of the delivery system) prior to crimping should dramatically reduce, if not eliminate, the degree of balloon bunching or compression affecting scaffold deployment during sheath fitting. Immediately after crimping, the proximally-placed sheath is moved from the balloon proximal end to the balloon distal end without causing balloon bunching damage, i.e., without causing folds in the balloon material to be essentially pulled towards the distal end as the sheath is being pulled from the proximal to distal end. Moreover, it was found that the method allowed the fitting of a sheath that possessed sufficient radial stiffness to restrain any radial recoiling of the scaffold when it is removed from the crimper head. A single piece sheath having about the same inner surface diameter as the outer surface diameter of the crimped scaffold and being radially stiff enough to prevent recoil can be pulled over a scaffold according to the invention without causing damage to the balloon. This desirable result was achieved for scaffolds longer than 18 mm and for scaffolds possessing a significant degree of strain energy when removed from the crimper (e.g., the scaffolds are radially compressed to at least 2.5 times their pre-crimp diameter but held at that diameter for well short of the time period needed within the crimp per head, e.g., about 30 minutes, to cause a significant degree of strain relaxation in the material). Thus, methods of the invention allow placement of a sheath over a scaffold possessing a high degree of strain energy, for purposes of restraining recoil, without causing damage to the balloon when the sheath is being fitted over the scaffold.

In some embodiments, another sheath, more easily removed from the scaffold (for the convenience of a physician or other medical specialist) is present over the scaffold prior to conducting the medical procedure. In this case a single layer sheath is used initially to reduce recoil and loss of retention. Then, after a period of time expires with the scaffold within the single piece sheath (e.g., about 30 minutes), the first sheath may be removed, e.g., by tearing it away from the scaffold, and replaced by a sheath that is more conveniently removed by a medical professional. The second sheath is a two-piece or one-piece sheath.

In a preferred embodiment, a first or temporary sheath is placed over the scaffold on a temporary basis, in order to address an immediate need for reducing recoil and loss of retention when the scaffold is removed from a crimp head of a crimping device. With the temporary sheath in place, the scaffold and balloon may then be examined to inspect the crimped scaffold or to perform other manufacturing process steps. Designed to restrain recoil immediately after crimping, removal of the temporary sheath can be more challenging or difficult to perform properly, especially for a medical specialist, technician or physician at the time when a sheath must be removed from the scaffold to initiate a medical procedure. As such, a second sheath (either one or two piece) may be designed as effectively or essentially less radially stiff so that it is more easily removable by a health professional. This may be preferred since following crimping there is strain relaxation. Hence, there is less radial stiffness required to prevent the scaffold from recoiling to a larger diameter after a period of time that the scaffold is within the first or temporary sheath.

It will be appreciated that in certain embodiments disclosed herein a scaffold must retain some memory in its material so that it can perform properly when expanded by the balloon. Unlike most metal stents, a polymer scaffold that relies on a radial expansion of the pre-cut tube for increased radial stiffness (as in a preferred embodiment) cannot be restrained in a crimped state so that it loses all radial stiffness properties that were induced in the pre-cut tube. If all this material memory is lost, scaffold struts become susceptible to cracking when the balloon is expanded within a lumen. Accordingly, methods of the invention also apply to restraints on polymer scaffolds but without totally eliminating radial strain energy within the crimped material, which is relied on to maintain structural integrity when the scaffold is radially expanded back to near its pre-crimp diameter.

According to the disclosure a delivery assembly is made for scaffolds that are introduced into the body without a sheath over the scaffold. So that the least amount of recoil occurs prior to introducing the scaffold into the body, it is preferred that the scaffold be within a sheath up until the point when the medical procedure is about to occur. Thus, it is desirable to have the scaffold and balloon retained within a sheath when packaged and the medical professional remove the sheath at the time of the medical procedure. To achieve this goal, the scaffold should be restrained within a sheath that may be easily removed and/or intuitively removed correctly by a medical professional. According to some embodiments, a one piece sheath may not be best suited to serve the needs of easy removal by a medical professional.

As such, according to another aspect of invention there is a method for making or assembling a delivery system. The method includes placing a first sheath over a scaffold when the scaffold is removed from a crimp head, removing this sheath and placing a second sheath over the scaffold and balloon, packaging the delivery assembly including the scaffold within the second sheath, sterilizing the packaged delivery system to produce a packaged medical device for use by the medical professional. The packaged medical device includes the scaffold within the second sheath, which is adapted for removal by the medical professional prior to introducing the scaffold into the body.

Embodiments of the second sheath are found in U.S. application Ser. No. 13/165,662 and may include a one or two piece design. The later type, a sheath pair, may be removed by a medical specialist such as a doctor without risk of the scaffold becoming dislodged from the balloon or damaged, such as when the sheath pair is accidentally removed in an improper manner by a health professional. The second sheath also provides an effective radial constraint for preventing recoil in a crimped scaffold, yet is comparatively easy to manually remove from the scaffold. A sheath that applies a radial constraint can be difficult to remove manually without damaging the crimped scaffold, dislodging or shifting it on the balloon. In these cases it is desirable to arrange the sheaths in a manner to apply an effective radial constraint yet make the sheaths capable of manual removal in a safe and intuitive manner. By making the sheath removal process easy to follow and intuitive, the possibility that a health professional will damage the medical device when removing the sheath is reduced. In one embodiment, the scaffold is constrained by a second sheath formed by a protecting sheath and a constraining sheath, as described in U.S. application Ser. No. 13/118, 311. The protecting sheath, or protecting portion, protects the integrity of the crimped scaffold-balloon structure while the constraining sheath or constraining portion, is applied and/or removed from the crimped scaffold. Arranged in this manner a radial inward force may be applied to a crimped scaffold via a sheath, without risking dislodgement or shifting of the scaffold on the balloon when the sheath is manually removed.

According to another embodiment, a sheath is placed over a scaffold to avoid bunching of balloon material and includes any of the crimping steps disclosed in FIGS. 3A-4A as described in application Ser. No. 13/644,347.

According to embodiments where two sheaths are used, e.g., a first sheath imposing a high radial stiffness and a second sheath imposing, effectively, a lower radial stiffness (to facilitate more easy removal by a health professional) the second sheath encompasses sheaths having a constraining and protecting portion, wherein the constraining portion applies a radial inward force and the protecting portion is disposed between the scaffold surface and the constraining portion. The constraining and protecting portion of the second sheath may be separate portions of a single sheath, or two separate sheaths that cooperate with each other to facilitate a restraint on recoil while allowing the sheath to be easily removed by a medical professional, e.g., removing the constraining portion prior to removing the protecting portion from the scaffold.

In accordance with the foregoing objectives, in one aspect of the invention there is a first method for assembling a scaffold-balloon catheter, comprising providing a catheter including a shaft and a balloon having distal and proximal ends; disposing a temporary sheath on the catheter shaft; crimping a polymer scaffold to the balloon while the sheath is disposed on the catheter shaft; advancing the temporary sheath from the balloon proximal end towards the balloon distal end to radially constrain the crimped scaffold; inspecting the crimped scaffold and/or balloon within the temporary sheath; removing the temporary sheath from the crimped scaffold; and placing a final sheath over the crimped scaffold.

In other embodiments the first method may include one or more of, or any combination of the following features as will be understood from one of ordinary skill in the art: wherein the scaffold is configured for being placed within a body only after the final sheath is removed; wherein the catheter is sealed within packaging while the crimped polymer scaffold is disposed within the final sheath; wherein the inspecting step includes increasing the pressure inside of the balloon, decreasing the pressure within the balloon then removing the temporary sheath from the crimped scaffold; wherein the temporary sheath is made from a transparent material and the inspecting step includes at least visually inspecting the crimped scaffold while disposed within the temporary sheath; wherein the temporary sheath is tubular having first and second ends, the first end is proximal the balloon proximal end and the second end is distal the balloon proximal end, and at least the second end is flared; wherein the constraining step includes deforming a flared end of the temporary sheath to reduce resistance to a sliding of the temporary sheath over the crimped scaffold; wherein both ends of the temporary sheath are flared and an end disposed adjacent the balloon has weakened portion to facilitate removal of the temporary sheath from the scaffold by tearing the temporary sheath at the weakened portion.

In another embodiment a second method for assembling a medical device includes providing a catheter including a polymer scaffold crimped to a balloon; and constraining the scaffold including placing a first sheath over the scaffold; removing the first sheath from the scaffold; and after removal of the first sheath, placing a second sheath over the scaffold.

In other embodiments the second method may include one or more of, or any combination of the following features as will be understood from one of ordinary skill in the art: wherein the second sheath applies a radial inward force on the crimped scaffold to limit recoil of the scaffold, extends distally of the catheter distal end by about a length equal to the length of the scaffold, and wherein the medical device is configured for being passed through the body of a patient only after the second sheath is removed; wherein the sheath comprises a protecting sheath and a constraining sheath that is placed over the protecting sheath and the crimped scaffold to limit recoil of the scaffold by an applying an inwardly directed radial force on the crimped scaffold; wherein the protecting sheath includes a first and second separable half forming a proximal portion of the constraining sheath; wherein the second sheath includes a protecting portion disposed over the scaffold, the first portion including an extension that is distal of the catheter distal end; and a constraining portion disposed over the scaffold and applying a radial-inward force on the scaffold; and wherein the scaffold is configured for being placed within a body only after the second sheath is removed.

In another embodiment a third method includes providing a balloon catheter, a scaffold and a sheath disposed on a shaft of the balloon catheter between a catheter proximal end and a balloon proximal end; crimping a polymer scaffold to the balloon-catheter; positioning the sheath over the crimped scaffold including moving a distal end of the sheath towards a balloon distal end.

In other embodiments the third method may include one or more of, or any combination of the following features as will be understood from one of ordinary skill in the art: the sheath is a first sheath made from at least a semi-transparent material, further including the steps of inspecting the scaffold and balloon within the first sheath, after inspecting the scaffold, removing the first sheath from the scaffold, then placing a second sheath over the scaffold to minimize recoil of the scaffold, wherein the medical device is configured for being passed through a body only after the second sheath is removed from the scaffold; wherein the first sheath is tubular and has a weakened portion at a distal end thereof; wherein the polymer has a lower end of a glass transition temperature TG-LOW and the crimping step includes heating the polymer to a temperature of about 5-15 degrees Celsius below TG-LOW; wherein the scaffold is crimped using an iris-type crimper mechanism; wherein the temporary sheath is positioned by restraining the catheter shaft while the temporary sheath is pulled towards the balloon distal end, wherein the pulling step includes depressing a flared end of the temporary sheath so as to avoid shifting of balloon material while the temporary sheath is being positioned over the scaffold; wherein the first sheath is placed by restraining the catheter shaft while the first sheath is pulled towards the balloon distal end, wherein the pulling step includes depressing a flared end of the first sheath so as to avoid shifting of balloon material while the first sheath is being placed over the scaffold; wherein the first sheath is positioned by restraining the catheter shaft while the sheath is pulled towards the balloon distal end, wherein the pulling step includes depressing a flared end of the sheath so as to avoid shifting of balloon material when the temporary sheath is being positioned over the scaffold; wherein the crimping step includes inflating or over inflating the balloon then at least partially crimping the scaffold to the balloon, and wherein the medical device is configured for being passed through a body only after the sheath is removed from the scaffold; and wherein prior to crimping, the scaffold has a first diameter that is greater than or equal to a fully or over-inflated balloon diameter.

In another embodiment there is a method for making a medical device, comprising providing a scaffold formed from a radially-expanded tube and having a pre-crimp diameter, the radially-expanded tube comprising a polymer; crimping the scaffold to a balloon catheter, the scaffold being crimped from the pre-crimp diameter to a final diameter, the pre-crimp diameter being at least 2 times the final diameter; placing the crimped scaffold within a first sheath by pulling the first sheath towards a distal end of the balloon catheter so that the crimped scaffold is disposed within the first sheath, the first sheath having a first diameter and a first radial stiffness sufficient to restrain recoil of the scaffold after crimping; replacing the first sheath with a second sheath having a second diameter and a second radial stiffness, the second sheath capable of being removed from a scaffold by a medical professional; wherein the scaffold is configured for being placed within a body only after the second sheath is removed from the crimped scaffold; and wherein the first diameter is less than the second diameter and/or the first radial stiffness is greater than the second radial stiffness.

In other embodiments the first method may include one or more of, or any combination of the following features as will be understood from one of ordinary skill in the art: the polymer is PLLA or a polymer, co-polymer or polymer blend comprising PLLA, the scaffold has a length of over 18 mm, greater than 100 mm or between 100 and 180 mm; the second sheath is a one or two-piece sheath; the second sheath has a constraining and protecting portion; and/or the first sheath has a fluted end disposed near a proximal end of the balloon.

INCORPORATION BY REFERENCE

All publications and patent applications mentioned in the present specification are herein incorporated by reference to the same extent as if each individual publication or patent application was specifically and individually indicated to be incorporated by reference. To the extent there are any inconsistent usages of words and/or phrases between an incorporated publication or patent and the present specification, these words and/or phrases will have a meaning that is consistent with the manner in which they are used in the present specification.

DETAILED DESCRIPTION OF EMBODIMENTS

A medical device according to a preferred embodiment includes a polymer scaffold formed from a radially expanded or biaxially expanded extruded PLLA tube, which is crimped to the balloon of a balloon catheter. The scaffold is laser cut from the expanded tube. The diameter of the tube is preferably selected to be about the same, or larger than the intended deployed diameter for the scaffold to provided desirable radial strength characteristics, as explained earlier. The scaffold is then crimped onto the balloon of the balloon catheter. Preferably, an iris-type crimper is used to crimp the scaffold to the balloon. The desired crimped profile for the scaffold is ½ or less than ½ of the starting (pre crimp) diameter of the expanded tube and scaffold. In the embodiments the ratio of the starting diameter (before crimping) to the final crimp diameter may be 2:1, 2.5:1, 3:1, or higher.

The pre-crimp memory in the scaffold material following crimping will induce some recoil when the scaffold is removed from the crimper. While a dwell period within the crimper can reduce this recoil tendency, it is found that there is residual recoil that needs to be restrained while the scaffold is awaiting use. This is done by placing a restraining sheath over the scaffold immediately after the crimper blades are released and the scaffold removed from the crimper head. This need to reduce recoil is particularly evident when the diameter reduction during crimping is high, since for a larger starting diameter compared to the crimped diameter the crimped material can have higher recoil tendencies.

Figure 1A:
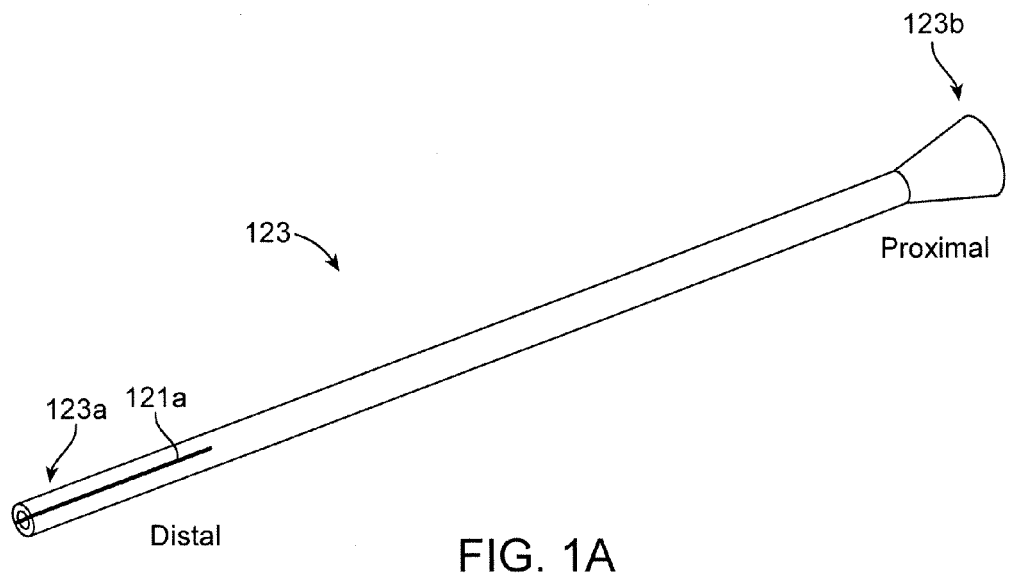
FIG. 1A is a perspective view of a first sheath for being placed over a crimped scaffold following crimping in order to reduce recoil of the scaffold.

According to one aspect of the embodiments, there is a solution to a problem, as discovered in detail below, when crimped scaffolds are placed within a restraining sheath to minimize recoil. For example, sheath 123 depicted in FIG. 1A, is placed over a crimped scaffold immediately following crimping to minimize recoil of the scaffold from its final crimped state to a larger diameter. As mentioned earlier, minimization of recoil is needed to maintain a low crossing profile and maintain the desired scaffold-balloon retention force which prevents the scaffold from being pulled off the balloon during delivery of the scaffold to a vessel site.

Figure 1B:
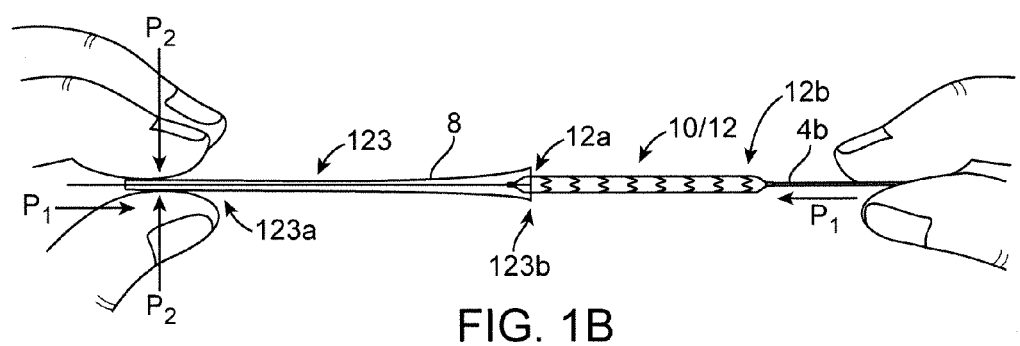
FIG. 1B depicts a procedure for placing the sheath of FIG. 1A over a crimped scaffold.
Figure 1C:
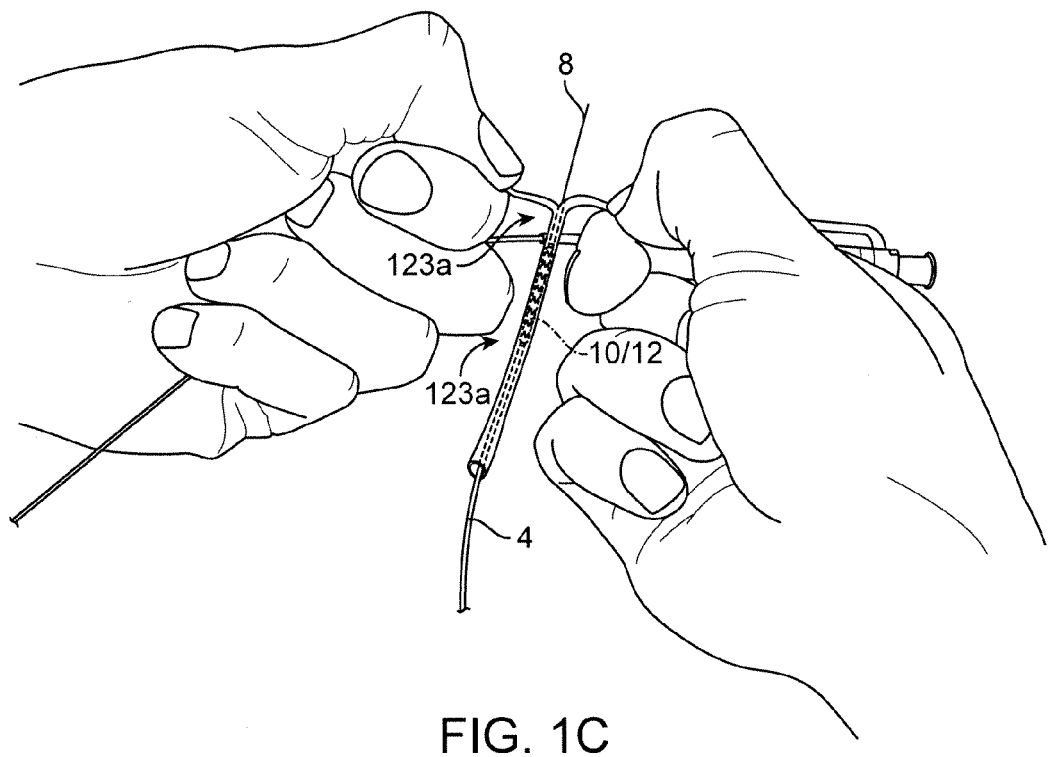
FIG. 1C depicts a procedure for removing the sheath of FIG. 1A from the scaffold.

The sheath 123 has a fluted or flared part at its proximal end 123b (to make more easy to align the distal end of the catheter with the opening of the sheath or insert the guiding mandrel or guide wire into the sheath) and a weakened portion (e.g., a slit 121a) formed at its distal end 123a. Referring to FIG. 1B, the sheath 123 is placed over the scaffold-balloon 10/12 disposed at a distal end of the catheter 2 by pushing the sheath proximal end 123b towards the balloon proximal end 12b (i.e., the end of the balloon 12 nearest the catheter 2 proximal end, which is not shown). Once placed, the sheath 123 is removed from the scaffold-balloon 10/12 (the scaffold 10 crimped to the balloon 12 is "scaffold-balloon 10/12") by tearing the sheath 123 away from the scaffold-balloon 10/12', as depicted in FIG. 1C. A user grips the sheath distal end 123a and pulls opposing portions of the sheath 123 apart along the weakened portion 121a.

Referring again to FIG. 1B, an operator placing the sheath 123 over the crimped scaffold 10/12 may proceed in the following fashion. First, a guide wire or mandrel 8 is disposed within the catheter 2 lumen and extends outwardly from the balloon distal end 12a. The tip of the mandrel 8 is then fed through the sheath 123 via its proximal end 123b and exits from the sheath distal end 123a. Next, as diagramed in the figure, the operator grips with the right hand the catheter shaft 2 and with the left hand the sheath 123. Holding the sheath 123 in place with the left hand, the operator pushes with the right hand the scaffold-balloon 10/12 into the sheath 123 lumen.

Since the sheath 123 is being used to prevent recoil, it is expected to have a relatively snug fit over the scaffold-balloon 10/12. Accordingly, there is often a fair amount of resistance encountered when the scaffold-balloon 10/12 is being pushed into the sheath 123 lumen. The operator must therefore squeeze the sheath 123 to hold it in place (as indicated by forces P2 in FIG. 1B), as well as apply forces P1 to overcome the frictional (and/or radial elastic) forces between scaffold 10 and sheath 123 resisting placement of the scaffold-balloon 10/12 within the sheath 123. The operator would prefer to hold the sheath 123 nearer its distal end 123a than proximal end 123b, to avoid exerting excessive radial and/or longitudinal forces (via finger pressure) directly on the scaffold 10 as this might cause the scaffold 10 to slip from the balloon 12. However, there is insufficient columnar strength in the sheath 123 and mandrel 8 to allow the operator to apply finger pressure away from the scaffold/balloon 10/12. If the operator were to attempt the fitting in this way, there can be occasional buckling or folding-over of the sheath 123 when the axial compressive forces P1 are being applied to the sheath 123, as can be appreciated from FIG. 1B, unless the operator grips the sheath 123 relatively close to, if not directly over the scaffold and balloon 10/12.

It has been found that the operator's fitting procedure just described; that is, applying finger pressure to the sheath 123 close to, if not directly over the scaffold/balloon 10/12 (to avoid buckling of the sheath 123) in the manner just described can result in a combined radial inward force and longitudinal force (i.e., "longitudinal force" meaning a force acting generally parallel to the mandrel 8 axis in FIG. 1B), forces on the scaffold/balloon 10/12 that disrupt or compress balloon material towards the balloon's proximal end 12b.

Figure 1D:
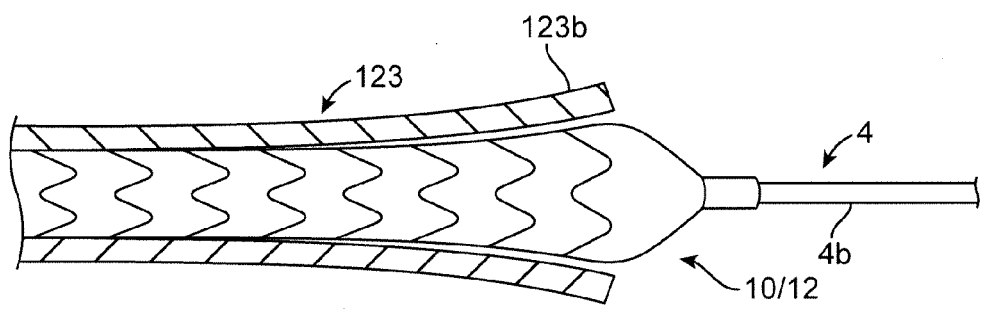
FIG. 1D is a cross-sectional view of the sheath of FIG. 1A when placed over the scaffold. In this figure there is shown balloon material bunching or compression near the proximal end of the scaffold caused by the sheath placement process.

FIG. 1D is intended to depict, in exaggerated form, a scaffold/balloon 10/12 within the sheath 123 when there is balloon bunching. The proximal end 12b of the balloon bulges, or has a larger diameter due to the pressing of balloon material towards the proximal end 12b. This is the result of the radial and longitudinal forces applied (via finger pressure) to, or near to the scaffold/balloon 10/12 when placing the scaffold/balloon 10/12 within the sheath 123. In this condition, the balloon 12 is susceptible to inflating improperly or even suddenly collapsing when inflated. Several solutions intended to avoid this problem were considered.

One potential solution is to increase the columnar strength of the sheath 123 by using a stiffer mandrel 8. However, it will be appreciated that this solution is not practical for several reasons. One being that the lumen size of the catheter 2 permits a mandrel diameter of limited size. A second possible solution is to use a sheath having a thicker wall or less compliant material than sheath 123. This is also not acceptable because the actual outer diameter of the scaffold 12 is not the same for all scaffolds in production. The outer diameter of the crimped scaffold 10 varies because the amount of scaffold recoil, from the time the scaffold is removed to the crimper until when the sheath 123 is placed over the scaffold, varies. Accordingly, the amount of force needed to push the sheath 123 over the scaffold will vary resulting in some scaffold being pulled off the balloon since the sheath 123 is less compliant. A third possible solution may be to expand radially the sheath 123 to a larger diameter, place the scaffold-balloon 10/12 within the deformed sheath 123, then heat shrink the sheath 123 back to its original diameter when the scaffold-balloon 10/12 lies within. While this approach may seem attractive, especially for a metal stent, it is not presently desirable for polymer scaffolds given the relative proximity of a polymer's glass transition temperature to the temperature needed to cause the sheath 123 material to return to its original, un-deformed diameter over the scaffold.

Figure 2:
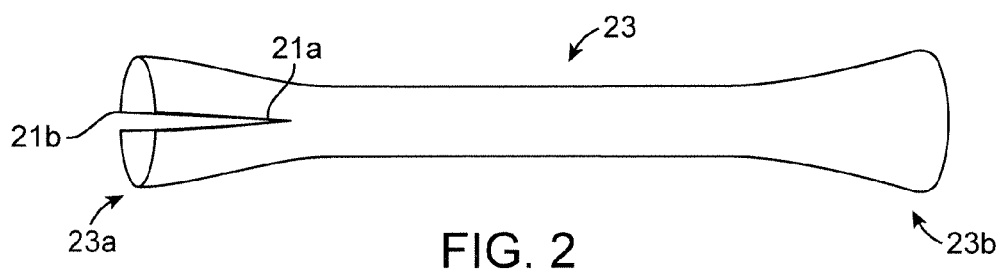
FIG. 2 is a perspective view of a second sheath for being placed over a crimped scaffold following crimping in order to reduce recoil of the scaffold and loss of retention between the scaffold and balloon. This sheath is also suited to not cause balloon bunching damage when pulled over a crimped scaffold.

FIG. 2 depicts a sheath 23 adapted for being placed over a scaffold to minimize recoil (post-crimp) while also reducing instances of balloon bunching as just discussed. Sheath 23 has a fluted end at both its proximal end 23b and distal end 23a. Additionally, sheath 23 has one or both of weakened areas 21a/21b, e.g., a slit, at the proximal end 23a, to facilitate tearing away of the sheath. Examples of polymers that may be used to construct sheath 23 are Pebax, PTFE, Polyethelene, Polycarbonate, Polyimide and Nylon. Examples of weakened portions, such as slits, for sheath 23 are described in U.S. application Ser. No. 12/916,349. Referring to FIGS. 3A-3E, there is depicted a process for placing crimping the scaffold 10 to the balloon 12 and then placing the scaffold-balloon 10/12 within the sheath 23 so as to minimize scaffold recoil (post-crimp) and avoid instances of balloon bunching described above. In a preferred embodiment the steps depicted in FIGS. 3A-3E are used in combination with sheath 23 to minimize recoil and avoid balloon bunching. Other embodiments may use the sheath 23 only, or the steps outlined above with a sheath similar to sheath 123.

Figure 3A:
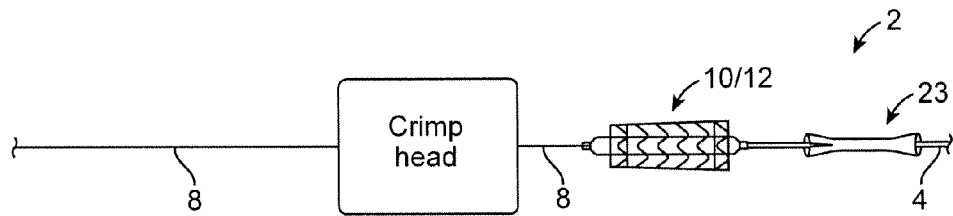
FIGS. 3A-3E depict steps associated with crimping and then placement of a sheath, such as the sheath of FIG. 2, over the crimped scaffold to minimize recoil and loss of retention while avoiding balloon bunching (FIG. 1D).

Referring to FIG. 3A, prior to crimping the sheath 23 is disposed over the catheter shaft 4 by sliding the sheath 23 over the balloon 12 starting from the balloon distal end 12a (left to right in FIG. 3A). The sheath 23 is then disposed between the proximal end 4b of the catheter shaft 4 (not shown) and the proximal end of the balloon 12b. The sheath 23 is disposed on the shaft 4 in this location during crimping. Next, the pre-crimp procedure for the scaffold 10 is initiated, which may include one or more of a deionization procedure for the scaffold 10, balloon 12 and/or crimper head, and/or inflation of the balloon 12 to its fully inflated state as discussed in U.S. application Ser. No. 12/916,349. The scaffold 10 and balloon 12 is then placed into the crimper head for crimping the scaffold 10 to produce the crimped scaffold-balloon 10/12.

Figure 3B:
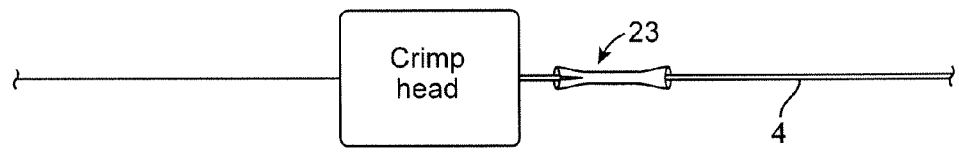

According to one embodiment, the steps of crimping the scaffold 10 to the balloon 20, as depicted in FIGS. 3A-3B, includes an additional step. In this embodiment the scaffold 10 is first crimped down to a smaller size using a temporary supporting balloon. After crimping the scaffold 10 using the temporary balloon (not shown) the temporary balloon is replaced with the balloon 12 of the balloon catheter as depicted in FIG. 3B. Further details of this embodiment are described in Applicant's co-pending application Ser. No. 13/644,347. The crimping steps set forth in FIGS. 3A and 4A of application Ser. No. 13/644,347 may be practiced for crimping a polymer scaffold to a balloon using the sheath 23 according to the invention.

Figure 3C:
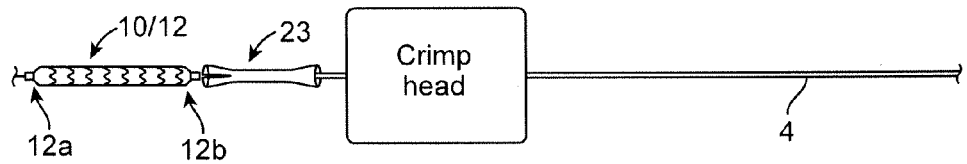
Figure 3D:
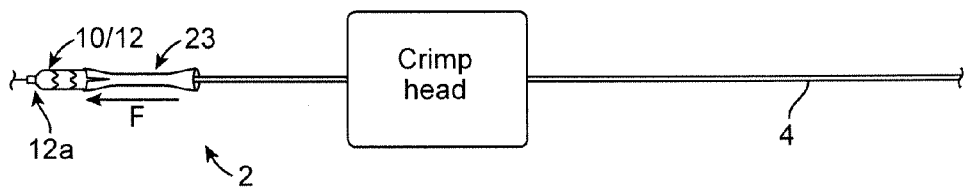

Referring to FIG. 3C, after completing the crimping process the scaffold is removed from the crimper head to the position shown, with the sheath 23 on the catheter shaft 4. The sheath 23 is then pushed over the scaffold-balloon 10/12, as indicated in FIG. 3D.

Figure 3E:
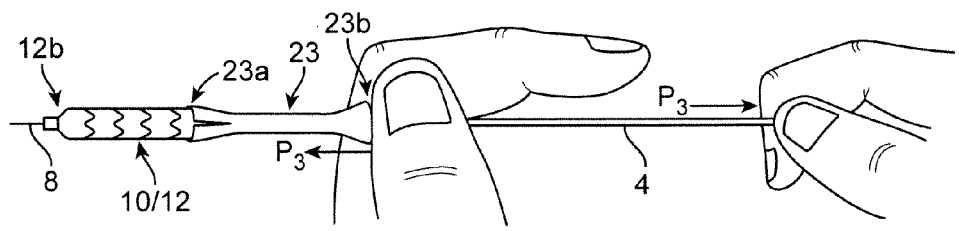

Referring to FIG. 3E, there is shown a more detail view of the manner in which a technician or operator may place the sheath 23 over the scaffold-balloon 10/12 when the sheath 23 is located on the catheter shaft 4, between the scaffold-balloon 10/12 and proximal end of the catheter prior to crimping. The operator grips the catheter shaft 4 with the right hand. The left hand is placed next to, or over the proximal end 23b of the sheath 23 and moved to the left, thereby causing, pushing, sliding or displacing the sheath 23 over the scaffold-balloon 10/12. The hands therefore exert forces P3 on the sheath 23 and shaft 4, approximately, to cause the sheath 23 to move over the scaffold-balloon 10/12.

Unlike the process discussed earlier in connection with FIGS. 1A-1C, now the operator benefits from the far stiffer catheter shaft 4 being used to advance the sheath 23 over the scaffold-balloon 10/12. As discussed earlier in connection with FIGS. 1A-1C, when the sheath 23 is advanced from the mandrel 8 end that is distal of the distal end 12a of the balloon 12, FIG. 1B, towards the proximal end 12b of the balloon 12 the operator needed to grip the sheath 123 more closely to, and tightly about the scaffold-balloon 10/12 (thereby sometimes causing balloon bunching at the proximal end 12b). With the arrangement shown in FIG. 3E, the catheter shaft 4 (being stiffer than the mandrel 8) may essentially be held by both hands to advance the sheath 23 over the scaffold-balloon 10/12. The advancement of the sheath 23 to the left in FIG. 3E requires less force on the scaffold-balloon 10/12, thereby resulting in less chance of balloon bunching, because the sheath 23 is better supported by the catheter shaft 4.

The sheath 23 further facilitates the avoidance of balloon bunching in its design. Both ends of sheath 23 are fluted or flared. The fluted distal end 23a allows a portion of the sheath 23 to extend over scaffold-balloon 10/12 prior to the narrower middle portion (between the fluted ends 23a/23b) engaging the scaffold 10 surface. Additionally the fluted distal end 23a makes it easier for an operator to grip the end 23a to initiate a tearing away of the sheath 23 at the weakened areas 21a/21b. By making it easier to tear away the sheath 23 there is less chance excessive finger pressure is inadvertently applied to the scaffold-balloon 10/12 within the sheath 23 when the sheath 23 is being torn away at the weakened portions 21a/21b.

The flared proximal end 23b offers advantages. By making this end, which is gripped (if only slightly) by the operator's fingers, flared, see FIG. 3E, the folding of this flared end 23a tends to place less radial pressure on the scaffold-balloon 10/12. The operator can more easily apply sufficient force to the sheath 23 to move it from left to right without having to squeeze as tightly the sheath 23 when a flared or enlarged proximal end 23b is provided. Indeed, it is believed that by squeezing a flared, verses non-flared end (as in the case of sheath 123) an elastic radial-outward reaction force tending to open-up the narrower middle portion (between flared ends 23a/23b) can occur, which tends to reduce the resistance to insertion of the scaffold-balloon 10/12 into the sheath 23 until the finger pressure is released.

Additionally, the sheath 23 length from end to end is preferably much longer than the length of the scaffold-balloon 10/12, e.g., extending over a length greater than the length between balloon markers, such as having the narrower middle portion approximately extend from one balloon marker to the other balloon marker so that the flared ends 23a and 23b extend from left and right, respectively, of the balloon markers. With this length sheath 23 an operator manipulating the sheath 23, when placing the sheath 23 over or removing the sheath 23 from the scaffold-balloon 10/12, there is less tendency for the operator to apply a radial inward force on the sheath 23 and near to the scaffold-balloon 10/12 while the sheath 23 is being pushed over the scaffold-balloon 10/12. As such, there is less chance of balloon bunching.

According to another aspect of the disclosure, there is a process for making a medical device including a polymer scaffold crimped to a balloon of a balloon catheter including using a temporary sheath to minimize recoil during the assembly process, followed by replacing the temporary sheath with a final sheath suited for being removed by a medical professional at the time of the medical procedure. It is preferred to use the sheath 123 for the temporary sheath; however, it is contemplated that other sheath designs may also be used for the temporary sheath, e.g., suitably chosen sheaths with or without weakened portions as described in U.S. application Ser. No. 12/916,349 and U.S. application Ser. No. 13/165,662.

Figure 4:
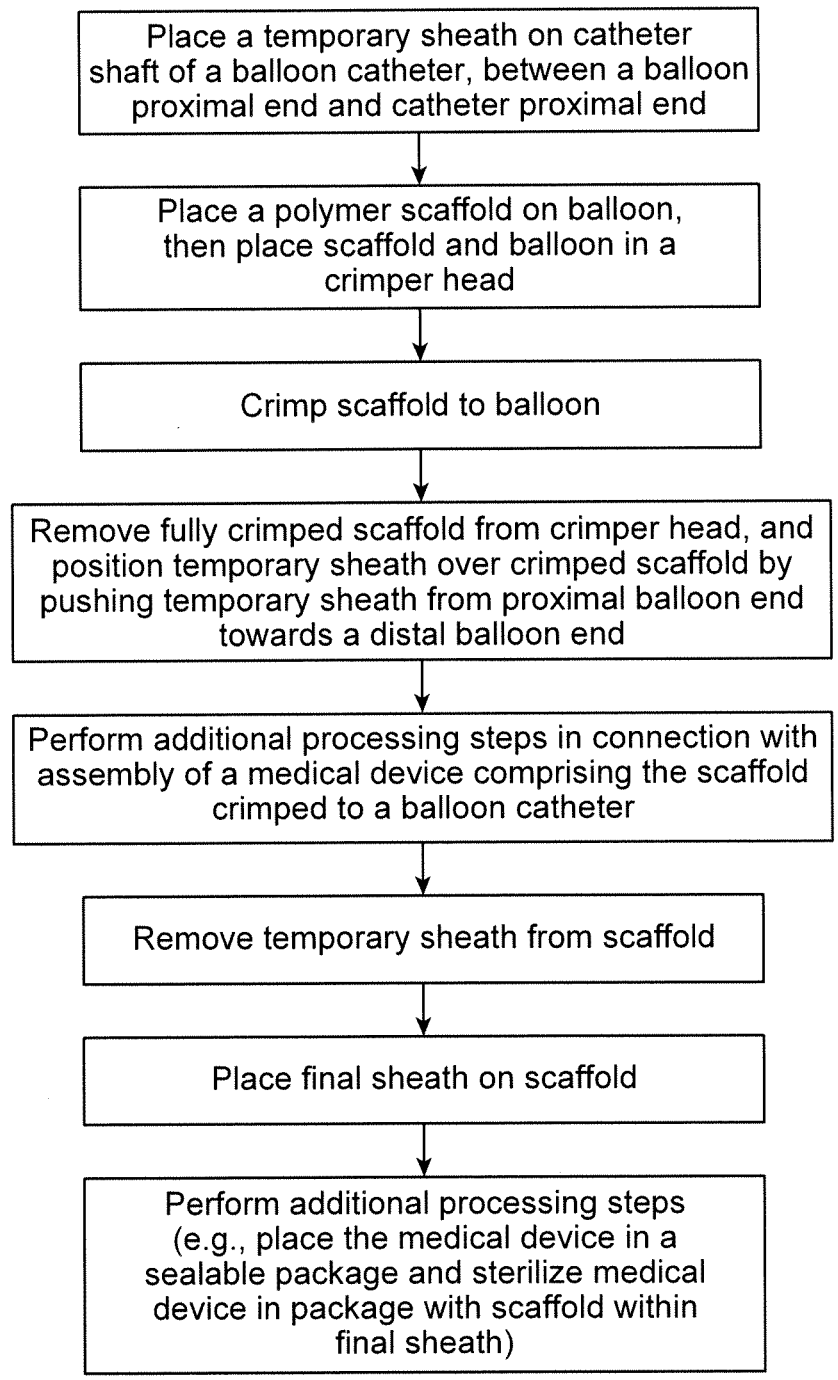
FIG. 4 is a flowchart depicting a process for assembling a medical device including crimping, placing a temporary sheath over a crimped scaffold, removing the temporary sheath, placing a final sheath over the crimped scaffold, packaging and then sterilizing the scaffold while the scaffold is within the final sheath.

FIG. 4 depicts steps involved in the assembly of a medical device, which includes a balloon catheter with a polymer scaffold crimped to the balloon of the catheter. First, a temporary sheath, e.g., sheath 23, is placed on the catheter shaft, the polymer scaffold is crimped to the balloon, and then the temporary sheath is placed over the scaffold. In preferred embodiments these steps are the same as those discussed earlier (including variants thereof) in connection with sheath 23 and FIGS. 3A-3E.

With the temporary sheath over the scaffold to minimize recoil, additional processing, testing or evaluation of the medical device may be done. Or the temporary sheath may be used to impose a relatively high radial restraint (as compared to a second or final sheath) to counteract recoil in the scaffold immediately after crimping. After there has been strain relaxation the temporary sheath may be replaced by a less stiff (or larger diameter), final sheath that is more easily removed by a health professional.

The temporary sheath is removed, e.g., as described earlier in connection with sheath 23, and replaced with a final sheath, such as the sheath illustrated in FIGS. 5-8, which is designed for removal by a medical professional, or someone less familiar with the precautions needed when removing a sheath so as to avoid displacing the crimped scaffold 10 from the balloon 12 or otherwise damaging the scaffold-balloon structure. The medical device with final sheath is then sealed in its packaging and sterilized, e.g., by E-beam sterilization. The final assembly includes a sterilized and sealed (in packaging) balloon catheter with polymer scaffold crimped to the balloon and the scaffold-balloon being contained within the final sheath.

A preferred embodiment of the final sheath, a two-piece sheath, including methods for placing it over the scaffold-balloon 10/12 and removal therefrom is described in FIGS. 5-8 and discussed in greater detail below.

Figure 5:
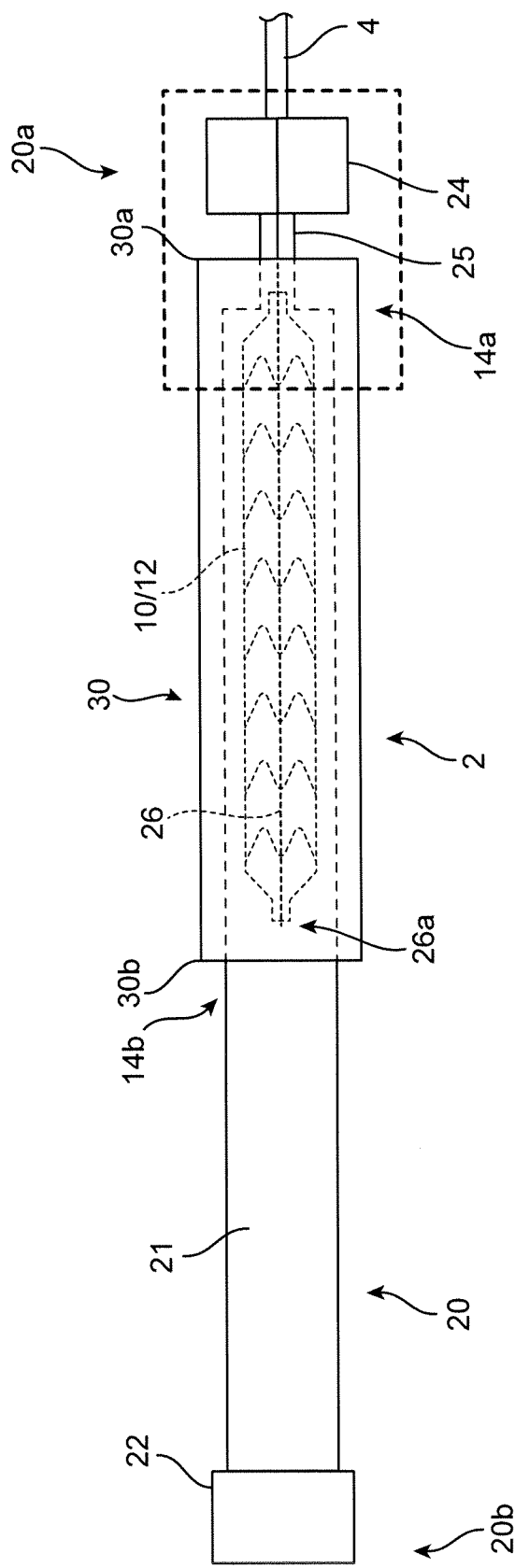
FIG. 5 is a side view of a polymer scaffold-balloon catheter assembly (medical device) with a pair of sheaths placed over the crimped scaffold. The sheath illustrated is one example of a final sheath adapted for being removed by a medical professional at the time when the scaffold will be introduced into the body.

FIG. 5 shows a side view of a distal portion of a scaffold-balloon catheter assembly 2. The catheter assembly 2 includes a catheter shaft 4 and a scaffold 10 crimped to a delivery balloon 12. As shown there are two separate sheaths 20, 30 disposed over the scaffold 10. The scaffold 10 is contained within a protecting sheath 20 and a constraining sheath 30, which is slid over the outer surface of the protecting sheath 20 to position it over the scaffold 10. Before inserting the catheter assembly 2 distal end within a patient, both the constraining sheath 30 and protecting sheath 20 are removed by a health professional.

The sheaths 20, 30 provide an effective radial constraint for reducing recoil in the crimped scaffold 10. Yet the sheaths 20, 30 are also easily removed by a health professional at the time of a medical procedure by pulling the outer sheath 30 towards the distal end of the scaffold 10 and balloon 12. This action will be described in more detail later. It is a similar motion to the removal technique required for other coronary device products, where a single, non-constraining sheath is used to cover and protect the stent. In those cases the sheath is grasped by the doctor or technician's gloved hands and pulled off towards the distal end of the device. A sheath that applies a radial constraint can be difficult to manually remove without adversely affecting the structural integrity of the medical device. In these cases, it is desirable to arrange the sheaths so that special handling is not required by the health professional when the sheath is manually removed. By making the sheath removal process easy to follow or intuitive, the possibility that a health professional will damage the medical device by improperly removing the sheath is reduced.

The constraint imposed by the sheaths 20, 30 maintain the scaffold 10 at essentially the same, or close to the same diameter it had when removed from the crimping mechanism, i.e., the crimped crossing profile, which is needed for traversing tortuous vessels to deliver the scaffold 10 to a target location in a body. The sheath 30 is tightly fit over the sheath 20 and scaffold 10 so that the radial inward force applied on the scaffold 10 can prevent or reduce recoil in the scaffold 10. The health professional may then remove both sheaths at the time of the medical procedure. As such, any potential recoil in the scaffold 10 prior to using the medical device is minimized.

The sheath 30, although imposing a tight fit on the scaffold 10 (through sheath 30), can be easily removed by a health professional without risk of the scaffold 10 being accidentally pulled off of the balloon 12. This is accomplished by the manner in which the sheath 20 is positioned and removed from the scaffold 10. If there are excessive pulling forces on the scaffold 10 when sheaths are removed, the scaffold 10 may dislodge from a balloon 12, or shift on the balloon 12, thereby reducing scaffold-balloon engagement relied on to hold the scaffold 10 to the balloon 12.

When the scaffold 10 is constrained by sheath 30, as in FIG. 5, the constraining sheath 30 is located over the section of the protecting sheath 20 where the crimped scaffold 10 is found. This sheath 30 is made from a polymer tube material having a thickness and pre-stressed inner diameter size suitably chosen to cause the sheath 30 to apply a radially inward directed force on the scaffold 10. The thicker the tube and the smaller the pre-stressed inner diameter size for the sheath 30 the higher this constraint will be on the scaffold 10. However, the sheath 30 thickness should not be too thick, nor its inner diameter too small as this will make it difficult to slide the sheath 30 over, or remove the sheath 30 from the scaffold 10. If excessive force is needed to reposition the sheath 30, the scaffold 10 can dislodge from the balloon 12 or become damaged when the sheath 30 is moved.

If only the single sheath 30 were used to constrain the scaffold 10, i.e., the sheath 20 is not present, the amount of preload that the sheath 30 could apply to the scaffold 10 without affecting scaffold-balloon engagement would be limited. However, by introducing the protecting sheath 20 between the scaffold-balloon surface and sheath 30 the sheath 30 can impose a higher preload on the scaffold 10 without risk to the integrity of the scaffold-balloon engagement when the sheath 30 is applied to and/or removed from the scaffold 10. The protecting sheath 20 therefore serves to protect the integrity of the scaffold-balloon structure as the sheath 30 is repositioned relative to the scaffold 10.

Figure 7A:
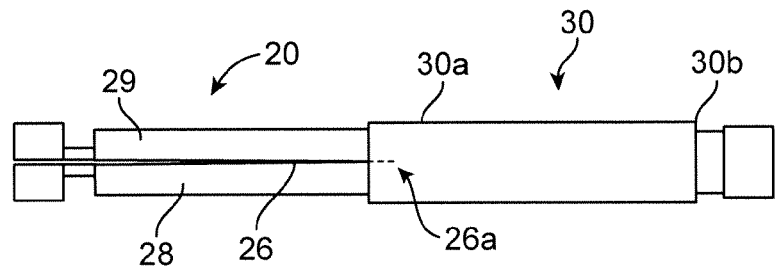
FIGS. 7A-7D illustrate a method of securing the sheath pair of FIG. 6A to a distal end of the catheter assembly of FIG. 5.
Figure 7B:
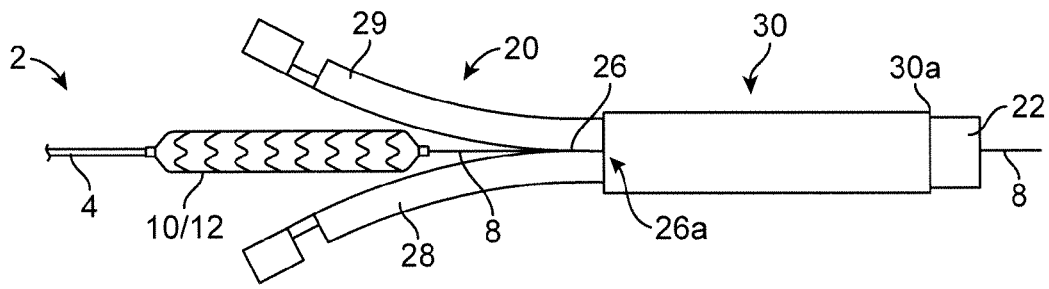
Figure 7C:
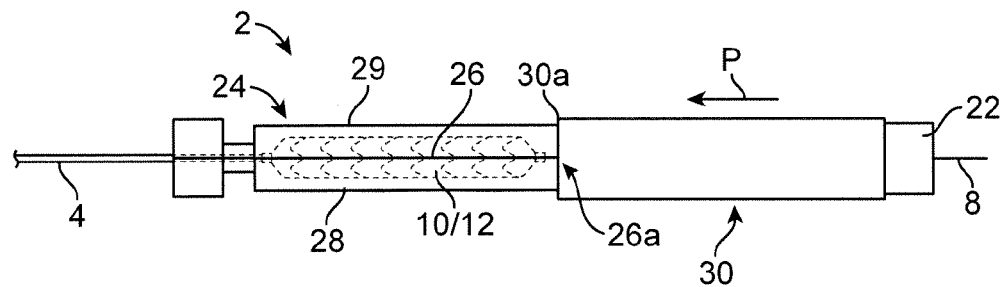

The protecting sheath 20 extends over the entire length of the scaffold (as shown) and beyond the distal tip of the catheter assembly 2 (i.e., the distal tip of the catheter assembly with sheaths 20, 30 removed, as can be more easily seen in FIGS. 7B and 7C), for reasons that will become apparent. The protecting sheath 20 is preferably formed from a unitary piece of polymer material, which is shaped to form differently sized portions 22, 24 and 25 for protecting the scaffold/balloon 10/12.

At the distal end 20b of sheath 20 there is a raised end 22 in the form of a cylinder section having a larger diameter than the body portion 21 of the sheath 20 to the right of end 22 which covers the scaffold 10 in FIG. 5. As such, raised end 22 provides an abutting surface with respect to distal movement of sheath 30, i.e., end 30b of sheath 30 abuts end 22 when sheath 30 is moved to the left in FIG. 5. End 22 may alternatively take the shape of a cone with the largest diameter end of the cone being the most distal end of the sheath 20. The raised end 22 is used to remove the sheaths 20, 30, as explained below.

The protecting sheath 20 has a cut 26, extending from the proximal end 20a to a location about at the distal the tip of the catheter assembly 2. The cut 26 forms an upper and lower separable halve 28, 29 of the sheath 20. These halves 29, 28 are configured to freely move apart when the sheath 30 is positioned towards the distal end 20b. The location 26a may be thought of as a living hinge 26a about which the upper half 29 and lower half 28 of the sheath 20 can rotate, or deflect away from the scaffold 10. When sheath 30 is moved distally of the scaffold 10 in FIG. 5, the halves 28, 29 will tend to open up naturally, due to the preload applied by sheath 30 near hinge 26a (the separable halves 28, 29 can be more clearly seen in FIGS. 6A-6D). This arrangement for halves 29, 28 allows sheath 20 it to be easily removed from the scaffold 10 with minimal disruption to scaffold-balloon structural integrity, after sheath 30 is moved to distal end 20b. When sheath 30 is being fitted over the scaffold 10 or removed from the scaffold 10, the presence of the halves 28, 29 prevent direct contact between the sliding sheath 30 and the surface of the scaffold 10.

At a proximal end 20a of sheath 20 there are portions 24 and 25 formed when the combined proximal ends of halves 28, 29 are brought together as in FIG. 5. When the halves 28, 29 are brought together the portions 24 and 25 take the form of a stepped or notched portion 25 and a raised end 24 similar to end 22, as shown in FIG. 5 and the cross-sectional view of the proximal end 20a of the assembly of FIG. 5A. The notched or stepped portion 25 has an outer diameter less than the outer diameter of the portion 21 of the sheath that covers the scaffold 10, as well as the outer diameter of the scaffold/balloon 10/12. The raised end 24 has a diameter that is greater than the body portion 21. The raised end 24 provides an abutment or stop 24a preventing the proximal end 30a of the sheath 30 from moving to the right in FIG. 5. As such, the end 24 prevents the sheath 30 from sliding off of the scaffold 10. The portion 24 also serves to identify the approximate location of the sheath 30 proximal end 30a so that it is fitted over the scaffold 10 and balloon 12. Sheath 30 has a length about equal to the length of the portion 25 plus the scaffold/balloon length so that when end 30a abuts end 24 the sheath 30 will properly cover the entire scaffold/balloon 10/12 length.

Figure 5A:
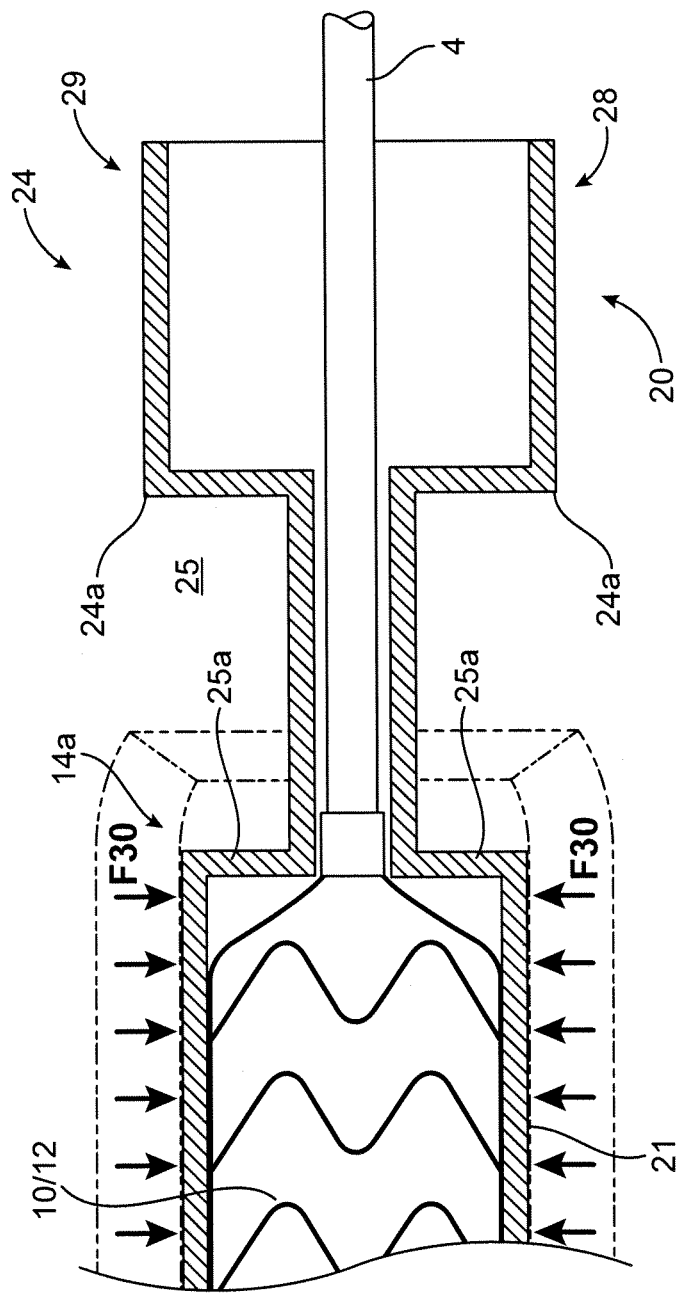
FIG. 5A shows a side view cross-section of a portion of the device of FIG. 5 at a proximal end thereof.

Portion 25 discourages removal of the sheath 20 prior to removal of sheath 30 from the scaffold 10. FIG. 5A shows a close-up of the proximal end 20a from FIG. 5 with the sheath 30 (shown in phantom) replaced by the inwardly directed preload F30 it applies to sheath portion 21 when positioned over the scaffold 10. A distal end of portion 25 forms a ledge 25a. When sheath 30 is positioned over the scaffold 10 the inwardly directed preload F30 applied to sheath portion 21 urges the halves 29, 28 together. With the halves 28, 29 urged together, the scaffold/balloon proximal end 14a blocks movement of the sheath 20 to the left in FIG. 5A by interfering with the movement of the ledge 25a to the left. Thus, if a user attempts to pull the sheath 20 off prior to removing the sheath 30 from the scaffold 10 area (which can damage the scaffold/balloon integrity), there will be resistance to this movement due to the ledges 25a abutting the balloon proximal end 14a (the ledge 25a thus may be thought of as an interference or interfering ledge part of the sheath 20). This resistance should indicate to the user that the sheaths 20, 30 are being removed in an improper manner. When the sheaths 20, 30 are removed properly, the first sheath 30 is moved to the distal end 20b of the sheath 20 (thereby removing the preload F30) so that the halves 28, 29 freely open up to allow the ledge 25a to easily pass over the scaffold 10 so that sheath 20 is removed without resistance. The user is thereby informed that the sheath 20 is removed properly when there is no resistance to removing the sheath 20 from the balloon-catheter assembly 2.

Thus, scaffold-balloon integrity is protected by the presence of the halves 28, 29 and the notched portion 25, as discussed above. The extended length of sheath 20, beyond the tip of the catheter assembly 2, e.g., is about equal to a length of the scaffold 10, the length of the sheath 30 or greater than both. This length beyond the distal tip facilitates an intuitive sliding removal or attachment of the sheath 30 from/to the scaffold 10 by respectively sliding the sheath 30 along the sheath 20 extension that is beyond the distal tip of the catheter assembly 2. The length of the sheath 20 that extends beyond the distal end 4 of the catheter assembly 2 (length L21 in FIG. 8A) may depend on the choice of sheaths used. For example, from the perspective of the health professional removal process, if the sheath 20 is more stiff (e.g., higher wall thickness and/or modulus) relative to the sheath 30 then the length beyond distal end 4 for sheath 20 may be longer so that the halves 28, 29 of sheath 20 can be more safely displaced from the scaffold 10 by clearing the sheath 30 more distally of the scaffold 10. If the sheath 30 wall thickness and/or modulus is higher relative to sheath 20 than the length may be shorter since the sheath 30 will tend to naturally open up the halves 28, 29 as it is moved distally of the distal tip of the catheter assembly 2. Also, a thicker or higher modulus sheath 20 and/or sheath 30 may be desirable to increase the resistance to improper removal of sheath 20, e.g., as when a user attempts to remove sheath 20 with, or before removing sheath 30 from the scaffold 10 (as discussed earlier).

Figure 6A:
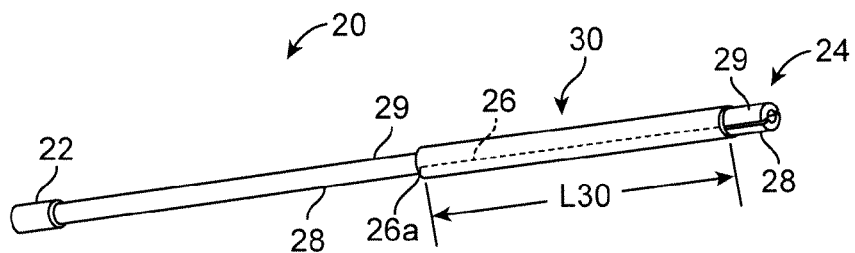
FIG. 6A is a perspective view of the sheath pair of FIG. 5.
Figure 6B:
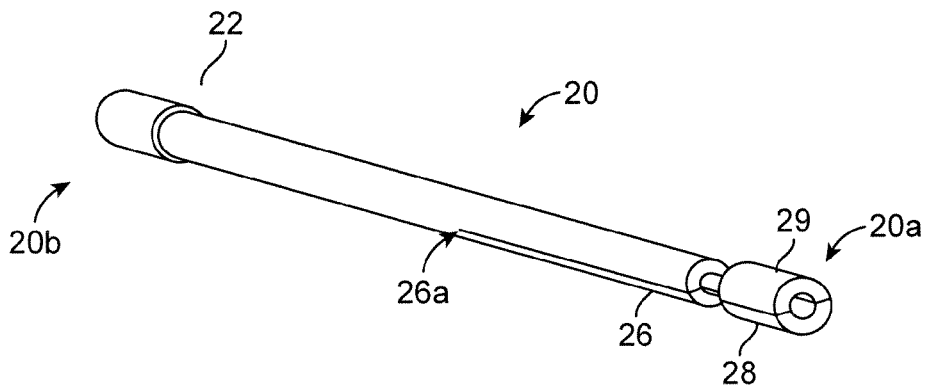
FIGS. 6B-6D show a side view, and first and perspective views of a protecting sheath of the sheath pair of FIG. 6A.
Figure 6C:
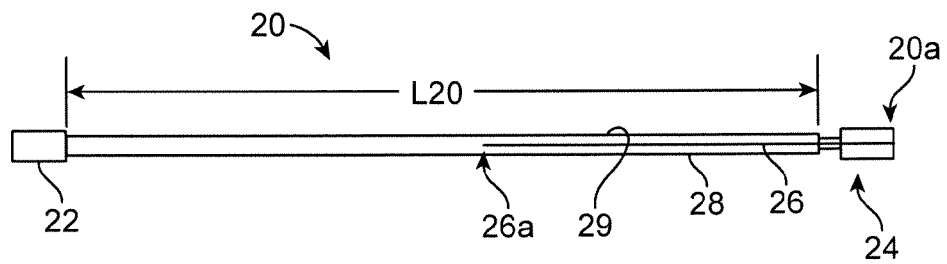
Figure 6D:
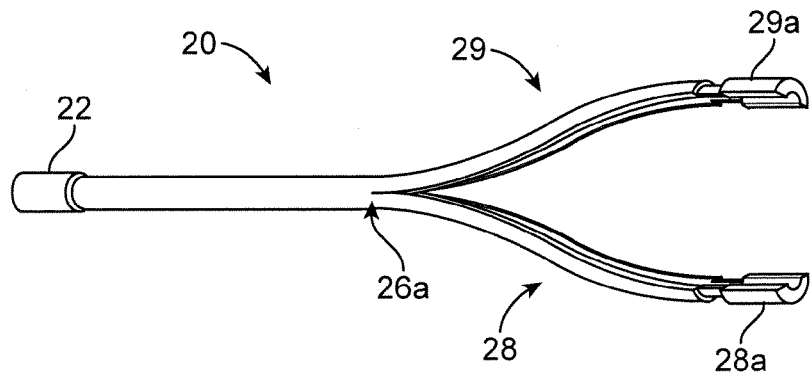

Referring to FIGS. 6B-6D, there are shown various views of the sheath 20. FIG. 6A shows the sheath 20 with the sheath 30. As mentioned above sheath 30 is sized to have a length L30 such that sheath 30 applies a sufficiently uniform radial inward force or preload on the scaffold 10 when end 30a abuts end 24a. The length L30 should therefore be slightly greater than the length of the scaffold-balloon structure. The sheath 30 can be slid towards or away from the scaffold location (i.e., its location in FIG. 6A or FIG. 5) over the sheath outer surface 20. As noted earlier, the sheath 20 has separable upper and lower halves 29, 28 formed by a cut 26 made across the tube forming sheath 20. FIG. 6D is a perspective view of the upper and lower halves 28, 29 separated from each other. As can be appreciated from this view, the halves 28, 29 rotate about the hinge 26a when they separate. FIGS. 6B and 6C show an additional side and perspective view, respectively, of the sheath 20 showing the aforementioned structure, including the portions of notched or stepped portion 25 and end 24 discussed earlier.

The length L20 in FIG. 6C should be chosen to extend over the scaffold 10 length as well as a sufficient distance beyond the scaffold 10 so that the sheath 30 can be pushed onto the scaffold 10, and removed from the scaffold 10 while the halves 28, 29 are disposed over the scaffold 10. The length L20 may be at least twice the length of sheath 30, i.e., L20=2*L30, to achieve this purpose. This length should be sufficient to allow the upper and lower halves 28, 29 to peel or rotate about the living hinge 26a and freely away from the scaffold surface (as in FIG. 6D) without interfering with the sheath 30.

As mentioned earlier, a thicker tube and smaller inner diameter for sheath 30 will cause the sheath 30 to apply a greater pre-load on the scaffold 10. The sheath 30 thickness and/or inner diameter size is selected with the sheath 20 in mind. That is, the sizing of one can determine what sizing to use for the other, based on achieving an appropriate balance among the amount of pre-load F30 (FIG. 5A) desired, the ease in which the sheath 30 can be placed over or removed from the scaffold 10 location, increasing resistance to improper removal of sheath 20 (ledge 25a abutting proximal end 14a, as discussed above) and avoiding disruption to the integrity of the scaffold-balloon structure, e.g., pulling the scaffold 10 off the balloon when the sheath 30 is being removed. For example, if a relatively thin and/or low modulus tube is used for sheath 20 (as compared to sheath 30), the sheath 30 will impose a higher localized pre-load on the scaffold 10. And the scaffold 10 is more likely to be affected by sheath 30 movement because the sheath 20 easily deforms under the movement of the sheath 30. If the sheath 20 is made thick and for a higher modulus tube material is used for sheath 20 (compared to sheath 30) the scaffold 10 will not be as affected by movement of the sheath 30. And local changes in pre-load on the scaffold 10 will tend to be lower since the sheath 20 does not deform as easily under the movement of the sheath 30.

Referring to FIGS. 7A-7D, methods of assembly using the sheaths 20, 30 (sheath pair) are now described. The scaffold 10 is crimped to the balloon 12 of the catheter assembly 2 using a crimping mechanism. As noted above, for a polymer scaffold the diameter reduction during crimping may be 2:1, 2.5:1, 3:1, 4:1 or higher. This diameter reduction introduces high stresses in the scaffold structure. The memory in the material following crimping causes recoil of the scaffold structure, as discussed earlier.

One can incorporate lengthy dwell times within the crimper, e.g., after the final crimp step, to allow stress-relaxation to occur in the structure while heated crimper blades are maintaining a fixed diameter and temperature to facilitate stress relaxation. Both the dwell period and the imposition of a constraining sheath over the crimped scaffold after crimping helps to reduce recoil after crimping. Crimping of the scaffold 10 to the balloon 12 including desirable dwell times and temperatures that can affect stress relaxation and recoil after crimping are disclosed in U.S. patent application Ser. No. 12/861,719, U.S. patent application Ser. No. 13/089,225 and U.S. patent application Ser. No. 13/107,666.

The sheath pair, shown in FIG. 7A, is placed on a mandrel 8 before being attached to the catheter assembly 2. The mandrel 8 is passed through the catheter shaft 4 guidewire lumen (not shown), and exits at the distal end of the catheter assembly 2. The sheath pair is then placed on the mandrel 8 distally of the catheter assembly 2. The mandrel 8 is then used to guide the sheath pair over the scaffold-balloon 10/12 as illustrated in FIGS. 7B-7D.

Referring to FIG. 7B, the distal end 30a of the sheath 30 is adjacent to the raised end 22 of the sheath 20. In this configuration the halves 28, 29 can freely open or close. The sheath pair is then brought towards the scaffold-balloon 10/12. The halves 28, 29 easily deflect over the scaffold-balloon 10/12. The sheath pair may be slid towards the scaffold-balloon 10/12 as follows. Holding the catheter assembly 2 stationary, grasping the mandrel 8 with one hand and the sheath pair with the other hand and sliding the sheath pair over the mandrel 8 until the halves 28, 29 are located over the scaffold-balloon 10/12 as shown in FIG. 7C. When properly positioned, the portions 24, 25 are positioned with respect to proximal end 14a as shown in FIG. 5A.

Figure 7D:
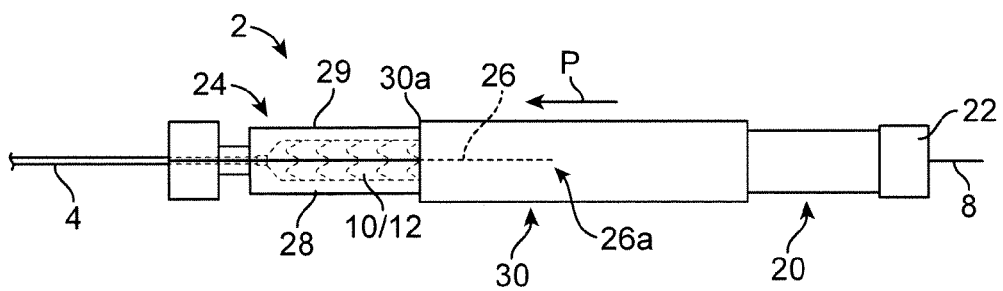

Referring to FIGS. 7C-7D, once the halves 28, 29 are located properly over the scaffold-balloon 10/12 to protect this structure, the constraining sheath 30 can be pushed over the scaffold-balloon 10/12 (as indicated in FIGS. 7C-7D by P). The sheath 30 may be pushed over the scaffold-balloon 10/12 in the following manner. The raised end 22 and mandrel 8 are grasped with one hand to hold the two stationary. Then, using the other hand the sheath 30 is pushed over the scaffold-balloon 10/12 until the end 30a of sheath 30 is disposed adjacent to, or abuts the raised end 24 of the sheath 20, which indicates the proximate location of the proximal end 14a of the balloon-scaffold 10/12. Alternatively, the portion 24 and catheter shaft 4 may be simultaneously held with on hand, while the sheath 30 is pushed towards the scaffold 10 with the other hand. By grasping the portion 24 with the catheter shaft 4, the halves 28, 29 are held in place relative to the scaffold 10 while the sheath 30 is being pushed over the scaffold 10.

Figure 8A:
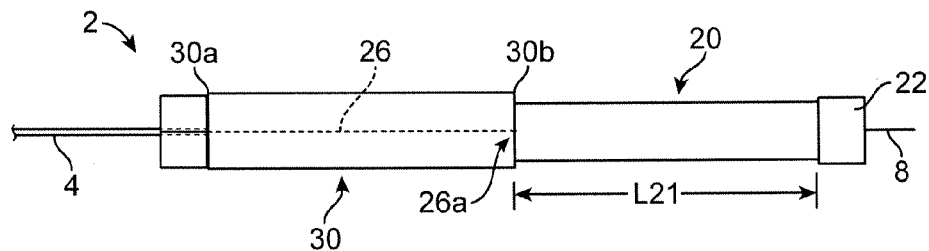
FIGS. 8A-8C illustrate a method of removing the sheath pair of FIG. 6A from the distal end of the catheter assembly of FIG. 5.

The catheter assembly 2 with sheaths arranged as in FIG. 8A is packaged and sterilized. At the time when the catheter assembly is to be used in a medical procedure the package is opened and the sheath pair removed from the distal end. The catheter assembly 2 is not configured for being introduced into the patient until the sheath pair is removed. FIGS. 5, 5A and 8A depict the arrangement of the sheaths 20, at the distal end of the catheter assembly 2 when the packaged and sterile medical device is received by a health professional. Examples of such sterile packaging is found in U.S. patent publication no. US 2008-0010947. The sheath 20 extends well-beyond the distal tip of the catheter assembly 2 such that it overhangs this distal tip. The overhanging portion of the sheath 20, which has a length of more than L21 (FIG. 8A), is provided to facilitate a safe and intuitive removal of the sheath pair by a health professional, thereby reducing the chances that the sheath pair are removed improperly.

Figure 8B:
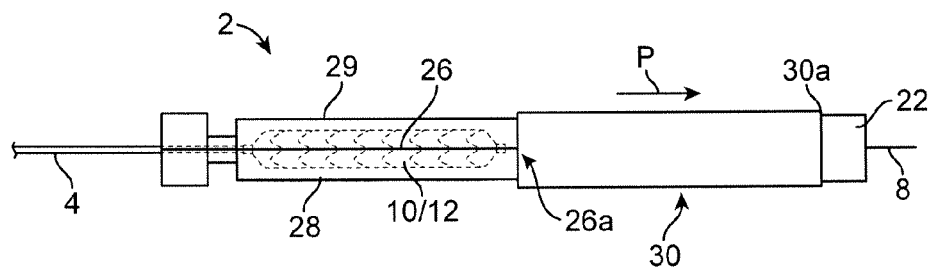
Figure 8C:
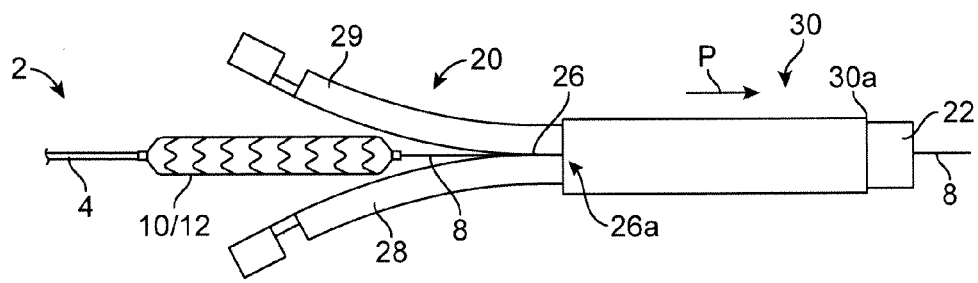

Referring to FIGS. 8B-8C, methods for removing the sheath pair from the scaffold-balloon 10/12 by the health professional are now described. These illustrations refer to moving the sheath pair over the mandrel 8; however, a mandrel 8 is not necessary. The sheath pair may be safely removed from the catheter assembly 2 without using a mandrel 8.

A sterilized and packaged catheter assembly with sheaths 20, 30 positioned as shown in FIG. 8A typically includes the stiffening mandrel 8 in the catheter shaft 4 lumen to provide bending stiffness for shaft 4. A distal end of the mandrel 8 has a curled end, or an extension/stop at the distal end (not shown), which is used to manually withdraw the mandrel 8 from the catheter shaft 4 lumen by pulling the mandrel 8 towards the distal tip of the catheter assembly 2. In the following example the sheaths 20, 30 are removed. The proscribed steps preferably also include the act of removing the mandrel 8 from the catheter shaft lumen by, e.g., simultaneously gripping the raised end 22, sheath 30 and mandrel 8.

First, the sheath 30 is pulled away from the scaffold-balloon 10/12 structure, where it is shown positioned in FIG. 8A. The sheath 30 may be withdrawn or pulled away from the scaffold-balloon 10/12 in the following manner. One hand grasps the raised end 22 and mandrel 8, to hold the two stationary, while the other hand grasps and pulls the sheath 30 towards the raised end 22. When the sheath 30 reaches the raised end 22 the halves 28, 29 should freely deflect away from the scaffold 10 surface, since a majority if not all of the cut 26 is to the left of the sheath 30 (FIG. 8B). At this point both sheaths 20, 30 can be simultaneously pulled away from the scaffold-balloon 10/12.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the claims should not be construed to limit the invention to the specific embodiments disclosed in the specification. Rather, the scope of the invention is to be determined entirely by the claims, which are to be construed in accordance with established doctrines of claim interpretation.

What is claimed is:

1. A method for assembling a medical device, comprising:
   providing a catheter including a shaft and a balloon having distal and proximal ends;
   disposing a temporary sheath on the catheter shaft;
   crimping a polymer scaffold to the balloon while the sheath is disposed on the catheter shaft;
   advancing the temporary sheath from the balloon proximal end towards the balloon distal end to radially constrain the crimped scaffold;
   inspecting the crimped scaffold and/or balloon within the temporary sheath;
   removing the temporary sheath from the crimped scaffold; and
   placing a final sheath over the crimped scaffold.

2. The method of claim 1, wherein the scaffold is configured for being placed within a body only after the final sheath is removed.

3. The method of claim 1, wherein the catheter is sealed within packaging while the crimped scaffold is disposed within the final sheath.

4. The method of claim 1, wherein the inspecting step includes increasing the pressure inside of the balloon, decreasing the pressure within the balloon then removing the temporary sheath from the crimped scaffold.

5. The method of claim 1, wherein the temporary sheath is made from a transparent material and the inspecting step includes at least visually inspecting the crimped scaffold while disposed within the temporary sheath.

6. The method of claim 1, wherein the temporary sheath is tubular having first and second ends, the first end is proximal the balloon proximal end and the second end is distal the balloon proximal end, and at least the second end is flared.

7. The method of claim 1, wherein the advancing step further includes deforming a flared end of the temporary sheath to reduce resistance to a sliding of the temporary sheath over the crimped scaffold.

8. The method of claim 1, wherein both ends of the temporary sheath are flared and an end disposed adjacent the balloon has a weakened portion to facilitate removal of the temporary sheath from the crimped scaffold by tearing the temporary sheath at the weakened portion.

9. The method of claim 1, wherein the temporary sheath is positioned by restraining the catheter shaft while the temporary sheath is advanced towards the balloon distal end,
   wherein the advancing step includes depressing a flared end of the temporary sheath so as to avoid shifting of balloon material while the temporary sheath is being advanced towards the distal balloon end.

10. A method for assembling a medical device, comprising:
    providing a catheter including a polymer scaffold crimped to a balloon; and
    constraining the scaffold including placing a first sheath over the scaffold;
    removing the first sheath from the scaffold; and
    after removal of the first sheath, placing a second sheath over the scaffold;
    wherein the first sheath is placed by restraining the catheter shaft while the first sheath is pulled towards a balloon distal end; and
    wherein the pulling step includes depressing a flared end of the first sheath so as to avoid shifting of balloon material while the first sheath is being placed over the scaffold.

11. The method of claim 10, wherein the second sheath applies a radial inward force on the scaffold to limit recoil of the scaffold,
    extends distally of the catheter distal end by about a length equal to the length of the scaffold, and
    wherein the medical device is configured for being passed through the body of a patient only after the second sheath is removed.

12. The method of claim 11, wherein the second sheath comprises a protecting sheath and a constraining sheath that is placed over the protecting sheath and the scaffold to limit recoil of the scaffold by applying an inwardly directed radial force on the scaffold.

13. The method of claim 12, wherein the protecting sheath includes a first and second separable half disposed between the scaffold and the constraining sheath.

14. The method of claim 10, wherein the second sheath includes
    a protecting portion disposed over the scaffold, the protecting portion including an extension that is distal of the catheter distal end; and
    a constraining portion disposed over the scaffold and the protecting portion and applying a radial-inward force on the scaffold.

15. The method of claim 10, wherein the scaffold is configured for being placed within a body only after the second sheath is removed.

16. A method for assembling a medical device, comprising:
    providing a balloon catheter, a scaffold and a sheath disposed on a shaft of the balloon catheter between a catheter proximal end and a balloon proximal end;
    crimping the scaffold to the balloon-catheter;
    positioning the sheath over the scaffold including moving a distal end of the sheath towards a balloon distal end, wherein the sheath is a first sheath made from a semi-transparent material,
    further including the steps of:
    inspecting the scaffold and balloon within the first sheath, after inspecting the scaffold, removing the first sheath from the scaffold, then placing a second sheath over the scaffold to minimize recoil of the scaffold, wherein the medical device is configured for being passed through a body only after the second sheath is removed from the scaffold.

17. The method of claim 16, wherein the first sheath is tubular and has a weakened portion at a distal end thereof.

18. The method of claim 16, wherein the scaffold comprises a polymer, wherein the polymer has a lower end of a glass transition temperature TG-LOW and the crimping step includes heating the polymer to a temperature of 5 to 15 degrees Celsius below TG-LOW.

19. The method of claim 16, wherein the scaffold is crimped using an iris-type crimper mechanism.

20. The method of claim 16, wherein the first sheath is positioned by restraining a catheter shaft while the first sheath is moved towards the balloon distal end, wherein the moving step includes depressing a flared end of the sheath so as to avoid shifting of balloon material while the temporary sheath is being moved towards the balloon distal end.

21. The method of claim 16, wherein the crimping step includes inflating or over inflating the balloon then at least partially crimping the scaffold to the balloon.

22. The method of claim 16, wherein prior to crimping, the scaffold has a first diameter that is greater than or equal to a fully or over-inflated balloon diameter.

23. A method for making a medical device, comprising:

providing a scaffold formed from a radially-expanded tube and having a pre-crimp diameter, the radially-expanded tube comprising a polymer;

crimping the scaffold to a balloon catheter, the scaffold being crimped from the pre-crimp diameter to a final diameter, the pre-crimp diameter being at least 2 times the final diameter;

placing the crimped scaffold within a first sheath by pulling the first sheath towards a distal end of the balloon catheter so that the crimped scaffold is disposed within the first sheath, the first sheath having a first diameter and a first radial stiffness sufficient to restrain recoil of the scaffold after crimping;

replacing the first sheath with a second sheath having a second diameter and a second radial stiffness, the second sheath capable of being removed from the crimped scaffold by a medical professional;

wherein the crimped scaffold is configured for being placed within a body only after the second sheath is removed from the crimped scaffold; and wherein the first diameter is less than the second diameter and/or the first radial stiffness is greater than the second radial stiffness.

* * * * *